United States Patent [19]

Stewart

[11] Patent Number: 4,830,855
[45] Date of Patent: May 16, 1989

[54] TEMPERATURE-CONTROLLED ACTIVE AGENT DISPENSER

[75] Inventor: Ray F. Stewart, Redwood City, Calif.

[73] Assignee: Landec Labs, Inc., Redwood City, Calif.

[21] Appl. No.: 120,399

[22] Filed: Nov. 13, 1987

[51] Int. Cl.[4] .................. A61F 13/02; A61K 9/14
[52] U.S. Cl. ..................... 424/448; 424/416; 424/449; 424/484; 424/486; 424/487
[58] Field of Search ............ 424/448, 449, 487, 486, 424/484, 416

[56] References Cited

U.S. PATENT DOCUMENTS

| | | | |
|---|---|---|---|
| 2,671,451 | 3/1954 | Bolger | 128/260 |
| 3,093,831 | 6/1963 | Jordan | 3/1 |
| 3,118,439 | 1/1964 | Perrenoud | 128/2 |
| 3,242,051 | 3/1966 | Hiestand et al. | 167/81 |
| 3,428,729 | 2/1969 | Anderson et al. | 424/19 |
| 3,485,235 | 12/1969 | Felson | 128/2 |
| 3,608,549 | 9/1971 | Merrill | 128/260 |
| 3,737,521 | 6/1973 | Born | 424/22 |
| 3,880,991 | 4/1975 | Yolles | 424/22 |
| 4,344,431 | 8/1982 | Yolles | 128/260 |
| 4,411,754 | 10/1983 | Kaetsu et al. | 424/487 X |
| 4,558,690 | 12/1985 | Joyce | 128/1 R |
| 4,657,543 | 4/1987 | Langer et al. | 604/891 |
| 4,666,441 | 5/1987 | Andriola et al. | 424/449 X |
| 4,675,174 | 6/1987 | Eckenhoff | 424/15 |
| 4,678,467 | 7/1987 | Eckenhoff et al. | 604/892 |
| 4,692,336 | 8/1987 | Eckenhoff et al. | 424/487 X |
| 4,729,904 | 3/1988 | Berthet et al. | 424/487 |

OTHER PUBLICATIONS

J. Polymer Sci.: Macromolecular Reviews (1974), 8:117.
J. Polymer Sci.: Polymer Chemistry Edition, vol. 19, 1871–1873. (1981).
Hackbarth, H. et al., Makromol. Chem., Rapid Commun. 7, 33–36 (1986).

*Primary Examiner*—Thurman K. Page
*Attorney, Agent, or Firm*—Irell & Manella

[57] ABSTRACT

Temperature-controlled diffusional active agent dispensers that use a side-chain crystallizable polymer in a form that is not free to flow above its melt temperature as a rate-controlling matrix are disclosed. The polymer may be crosslinked to render it nonflowable, be supported, or grafted to a permeable support. Elements that facilitate or permit heating by radiation or electrical conductance/inductance may be included in the dispenser. At temperatures below the melt temperature of the polymer, the polymer is substantially impermeable to the agent. At tempertures at or above the melt temperature the polymer is substantially permeable to the agent.

30 Claims, 1 Drawing Sheet

TEMPERATURE-CONTROLLED ACTIVE AGENT DISPENSER

TECHNICAL FIELD

This invention is in the fields of polymer chemistry and controlled release active agent dispensers. More particularly, it relates to the use of certain side-chain crystallizable polymers as diffusional matrices or membranes in making temperature-controlled active agent dispensers.

BACKGROUND ART

Controlled-release dispensers that operate on a diffusional mechanism are well known. In general, there are two basic types of such devices: one in which the agent to be dispensed is dispersed in an agent-permeable polymeric matrix; and the other in which the active agent is contained within a reservoir bounded wholly or partly by an active agent-permeable polymeric membrane. In both types of devices the agent dissolves in the polymer and diffuses through it to the surface of the dispenser and thence to the environment of use. Dispensers of this type have been used for dispensing a variety of active agents to environments of use, such as administration of drugs to animals, including humans, administration of agricultural chemicals to crops or pests, administration of chemicals to water for sanitation purposes, administration of fragrances to mask obnoxious odors, and administration of catalysts to chemical reactions. In general these prior dispensers have been temperature-insensitive except to the extent that the solubility of the agent in the polymer or the coefficient of diffusion varied with temperature. In the polymers used previously in diffusional-type dispensers this variation typically has not been significant.

The present invention uses a type of polymer called a side-chain crystallizable polymer as the diffusional barrier in diffusional-type active agent dispensers. These polymers exhibit permeability to molecules of interest that varies significantly as a function of temperature. These temperature-dependent permeation properties permit applicant to make temperature-sensitive dispensers which can be turned on and off by temperature variation or whose rate of release can be increased significantly by a temperature increase.

Several prior art references have involved the use of side-chain crystallizable polymers as elements in active agent dispensers. U.S. Pat. No. 3,608,549 describes a capsule for administering drugs. The wall of the capsule is made of a drug-permeable nonmelting elastomer such as silicone rubber. The core of the capsule consists of a meltable polymer matrix which contains the drug and a metal coil. The meltable matrix is described as a material which has a solid, crystalline state at low temperature in which it has a low coefficient of diffusion to the drug and a liquid state at higher temperatures in which it has a high coefficient of diffusion to the drug. The metal coil is heated by induction to cause the meltable matrix to become liquid and thus permeable to the drug. Once this occurs, the drug diffuses from the device at a rate controlled by its rate of diffusion through the nonmelting capsule wall. The patent lists several materials that melt at 40°–47° C., including one, poly(stearyl acrylate), that is a side-chain crystallizable polymer. The use of a meltable polymer in this patented device is, however, different in several respects from the use of side-chain crystallizable polymers in the present invention. In the present invention the side-chain crystallizable polymer is in the form of a body that retains its shape and does not become wholly liquid. Also, the side-chain crystallizable polymer is the primary release-rate controlling element in the present invention. Further, in most embodiments of the invention dispenser the side-chain crystallizable polymer is not an internal element of the dispenser but instead defines a surface that interfaces with the environment of use.

U.S. Pat. No. 4,558,690 describes an anticancer capsule comprising an anti-neoplastic agent encapsulated in a meltable polymer. Polyoctadecyl acrylate, a side-chain crystallizable polymer, is used as the meltable polymer. Once the composition has been delivered to the tumor, nonionizing radiation is used to locally heat the tumor and melt the capsule wall so that it disintegrates and permits the agent to be released by dissolution. In such a capsule, the polymer does not retain its shape and drug release does not occur via diffusion through the polymer. U.S. Pat. No. 3,242,051 mentions polyvinyl stearate, another side-chain crystallizable polymer, as a precoating material in a two-step microencapsulation process.

Macromol. Chem. Rapid. Commun. (1986) 7: 33–36 describes the permeation of alkanes through membranes composed of a $C_{16}$ methacrylate polymer (a side chain crystallizable polymer) dispersed in a polycarbonate or coated on a porous polysulfone as a function of temperature. Significant increases in alkane permeability were observed at the melting point of the $C_{16}$ methacrylate polymer with the membrane composed of the $C_{16}$ methacrylate polymer coated on a porous polysulfone support. This reference does not relate to temperature-controlled devices for dispensing active agents.

Crosslinked side-chain crystallizable polymers are described in J. Polymer Sci.: Macromolecular Reviews (1974) 8: 117 and J. Polymer Sci.: Polymer Chemistry Edition (1981) 19: 1871–1873. Applicant knows of no use of crosslinked side-chain crystallizable polymers as diffusion matrices.

DISCLOSURE OF THE INVENTION

Cone aspect of the invention is a temperature controlled agent dispenser that provides a reversible, substantial change in agent dispensing rate at a selected temperature comprising a body that maintains its integrity at the selected temperature and is comprised of an agent and a side-chain crystallizable polymer which (i) is in a form that retains its shape and is not free to flow at the selected temperature, (ii) exhibits a phase transition at the selected temperature, (iii) has substantially greater permeability to the agent at temperatures equal to or greater than the selected temperature than at temperatures below the selected temperature, and (iv) is interposed between the agent and an environment into which the agent is to be dispensed, whereby the rate at which the agent is dispensed to the environment at a temperature equal to or greater than the selected temperature is dependent upon the rate at which the agent diffuses therethrough.

Various structures that are useful as temperature-controlled diffusional matrices in regulating the transport of an active agent from a source of said agent to an environment of use for said agent and which include or comprise the above-described side-chain crystallizable polymer in a form in which it is immobilized and thus not free to flow at its melting temperature are another aspect of the invention.

One such structure comprises a diffusional matrix comprising a body of (a) a solid support phase and (b) a side-chain crystallizable polymer phase immobilized within the support phase which (i) exhibits a phase transition at a selected temperature and (ii) has substantially greater permeability to the agent at temperatures equal to or greater than the selected temperature than at temperatures below the selected temperature, wherein there is at least one continuous path through the body that is defined by the side-chain crystallizable polymer phase.

Another such structure comprises (a) a continuous agent-permeable polymer membrane and (b) the side-chain crystallizable polymer grafted to the surface of the membrane.

A third such structure is a laminated composite comprising (a) a layer of the side-chain crystallizable polymer sandwiched between (b) layers of an agent-permeable polymer wherein the layers of agent permeable polymer are bonded to each other at one or more sites to prevent relative motion therebetween.

MODES FOR CARRYING OUT THE INVENTION

Figure 1:
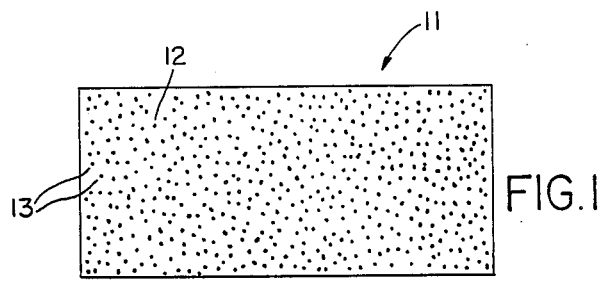
FIG. 1 is an enlarged cross-sectional view of one embodiment of this invention in which active agent is dispersed throughout a matrix of side-chain crystallizable polymer.

"Active agents" as used herein include those compositions of matter which when dispensed in their environment of use produce a predetermined, beneficial and useful result. Such agents include for example pesticides, herbicides, germicides, biocides, algicides, rodenticides, fungicides, insecticides, anti-oxidants, plant growth promoters and inhibitors, preservatives, surfactants, disinfectants, catalysts, enzymes, fermentation agents, nutrients, drugs, plant minerals, pheromones, sex sterilants, plant hormones, air purifiers, microorganism attenuators and the like.

The term "drug" as used herein broadly includes physiologically and/or pharmacologically active substances for producing a localized effect at the administration site or a systemic effect at a site remote from the administration site.

Side-chain crystallizable polymers, sometimes called "comb-like" polymers are well known and available commercially. These polymers are reviewed in J. Poly. Sci.: Macromol. Rev. (1974) 8: 117–253. In general these polymers may be represented by the formula

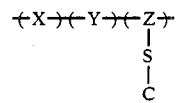

where X is a first monomer unit, Y is a second monomer unit, Z is a backbone atom, S is a spacer unit and C is a crystallizable group. The $M_w$ of C is equal to or greater than twice the sum of the $M_w$s of X, Y and Z. These polymers have a heat of fusion ($\Delta Hf$) of at least about 5 calories/g, preferably at least about 10 calories/g.

The backbone of the polymer (defined by X, Y and Z) may be any organic structure (aliphatic or aromatic hydrocarbon, ester, ether, amide, etc.) or an inorganic structure (sulfide, phosphazine, silicone, etc.). The spacer linkages can be any suitable organic or inorganic unit, for example ester, amide, hydrocarbon, phenyl, ether, or ionic salt (for example a carboxyl-alkyl ammonium or sulphonium or phosphonium ion pair or other known ionic salt pair). The side-chain (defined by S and C) may be aliphatic or aromatic or a combination of aliphatic and aromatic, but must be capable of entering into a crystalline state. Common examples are linear aliphatic side-chains of at least 10 carbon atoms, fluorinated aliphatic side-chains of at least 6 carbons, and p-alkyl styrene side-chains wherein the alkyl is of 8 to 24 carbon atoms.

The length of the side-chain moiety is usually greater than 5 times the distance between side-chains in the case of acrylates, methacrylates, vinyl esters, acrylamides, methacrylamides, vinyl ethers and alpha olefins. In the extreme case of a fluoroacrylate alternate copolymer with butadiene the side chain can be as little as 2 times the length as the distance between branches. In any case the side-chain units should make up greater than 50% of the volume of the polymer, preferably greater than 65% of the volume. Co-monomers added to a side chain polymer usually have an adverse effect on crystallinity. Small amounts of various co-monomers can be tolerated, usually up to 10 to 25 volume percent. In some cases it is desirable to add a small amounts of comonomers, for example cure site monomers such as acrylic acid, glycidal methacrylate, maleic anhydride, amino function monomer and the like.

Specific examples of side-chain crystallizable monomers are the acrylate, fluoroacrylate, methacrylate and vinyl ester polymers described in J. Poly. Sci. (1972) 10: 3347; J. Poly. Sci. (1972) 10: 1657; J. Poly. Sci. (1971) 9: 3367; J. Poly. Sci. (1971) 9: 3349; J. Poly. Sci. (1971) 9: 1835; J.A.C.S. (1954) 76: 6280; J. Poly. Sci. (1969) 7: 3053; Polymer J. (1985) 17: 991, corresponding acrylamides, substituted acrylamide and maleimide polymers (J. Poly. Sci., Poly. Physics Ed. (1980) 18: 2197; polyalphaolefin polymers such as those described in J. Poly. Sci.: Macromol. Rev. (1974) 8: 117–253 and Macromolecules (1980) 13: 12, polyalkylvinylethers, polyalkylethylene oxides such as those described in Macromolecules (1980) 13: 15, alkylphosphazene polymers, polyamino acids such as those described in Poly. Sci. USSR (1979) 21: 241, Macromolecules (1985) 18: 2141, polyisocyanates such as those described in Macromolecules (1979) 12: 94, polyurethanes made by reacting amine- or alcohol-containing monomers with long chain alkyl isocyanates, polyesters and polyethers, polysiloxanes and polysilanes such as those described in Macromolecules (1986) 19: 611 and p-alkylstyrene polymers such as those described in J.A.C.S. (1953) 75: 3326 and J. Poly. Sci. (1962) 60: 19.

The main properties of the side chain crystallizable polymer that are believed to affect its permeability properties are: melting point, glass transition, crystallinity, crosslink density, and side chain structure. Melting point will be chosen to correlate to the temperature at which release from the device via diffusion through the polymer is desired. For instance, if one desires a device for releasing a given agricultural chemical at 25° C. or above, a side chain crystallizable polymer having a melting point of approximately 25° C. is chosen. The percent crystallinity of the polymer (below its melt point) will typically be in the range of 10% to 55%, more usually 15% to 50%. In general, the higher the crystallinity, the greater the change in permeability exhibited at phase transition. As indicated below, the crosslink density will typically be greater than about 0.1 to 1. Crosslinking in general decreases permeability at melt. At such crosslink densities, however, the decrease is not sufficient enough to render the permeability of the polymer substantially insensitive to temperature but is sufficient enough to significantly reduce the fluidity of the polymer at temperatures above the melt temperature. As indicated above, the chemical structure of the polymer may vary widely. The permeability of the polymer will typically be at least twofold and more usually at least fivefold higher at or above its melting point than at temperatures below its melting point.

For use as a diffusional matrix in accordance with the invention, the side-chain crystallizable polymer is in a form in which it retains its shape and is not free to flow at its melting temperature (i.e., the temperature/temperature range at/over which the side chains undergo a phase change from crystalline to amorphous). Otherwise, the polymer would not remain in its intended location (interposed between the agent and the environment) and would be displaced or dispersed elsewhere due to gravitational or other forces. In this regard, in many embodiments the side-chain crystallizable polymer interfaces directly with the environment (its surface contacts the environment) and would be free at its melt temperature to disperse into the environment.

In one such form, the side-chain crystallizable polymer is crosslinked to a degree such that it becomes viscoelastic at its "melt" temperature but is not so fluid that it readily flows in response to mild forces. Accordingly, the term "crosslinked side chain crystallizable polymer" is used to describe side chain crystallizable polymers which are resistant to flow above their side chain melting points. Resistance to flow is obtained by providing sufficient crosslinking density that the material has an elastic modulus above the melting point of the side chains. Generally, crosslink density in these material is described as the number of crosslinks per weight average molecular weight. For example, a polymer having an average molecular weight of 125,000 and having an average of 1 intermolecular crosslink per polymer chain is stated to have a crosslink density of 1. In order for a side chain crystallizable polymer to resist flow above the melt it is desirable to have a crosslink density greater than about 0.1, preferably greater than 0.5 and most preferably greater than 1. It is not necessary for all of the polymer chains in a material to be crosslinked and a high gel content is not generally necessary unless the application requires great solvent resistance. Generally crosslinking beyond about 10 mole percent is not necessary under normal circumstances and excessive crosslinking can result in decreased crystallinity and impaired performance. In terms of mole percent the crosslinking will normally be in the range of 0.01 percent to 10 mole percent. The crosslinked polymers will normally have a heat of fusion of at least about 5 cal/g, more usually at least 8 cal/g.

A variety of methods are available to produce crosslinked side chain crystallizable materials for use in controlled release dispensers. A network co-polymer can be prepared by polymerizing a side chain crystallizable monomer and a multifunctional monomer either in one or two steps. A one step process may be used to form a membrane in place, while a two step process is useful where an intermediate processing step is necessary. A variety of multifunctional monomers (di, tri or multifunctional acrylic or methacrylic esters, vinyl ethers, esters or amides, isocyanates, aldehydes, epoxies and the like) are known in the art. These multifunctional monomers can be used in a one or two step process depending on the desired result. Ionizing radiation, for example beta or gamma radiation, peroxides, silanes or similar cure agents can be used to crosslink a preformed side chain crystallizable polymer with or without added co-monomers. Ionic crosslinks can be formed by for example reacting an acidic polymer site with a di- or tri-valent metal salt or oxide to produce a complex which serves as a crosslink site. Likewise organic salts or complexes can be prepared by methods known in the art.

Effective crosslinking may also be obtained by physical methods. For example a block co-polymer of a side chain crystallizable polymer and a second polymer which exhibits a glass transition or melting point higher than the side chain crystallizable polymer may be prepared wherein the entire mass exhibits mechanical stability above the melting point of the side chain crystallizable polymer but below the transition of the second polymer.

In another form the side-chain crystallizable polymer is placed within a support such as a microporous membrane, hollow fiber or fabric mesh. In such embodiments the polymer is immobilized by physical entrapment, surface tension, and/or other physical forces. The side-chain crystallizable polymer fills the pores of the membrane or holes in the mesh, thus providing numerous continuous pathways of side-chain crystallizable polymer through the membrane/mesh. The polymer may be placed in the pores/holes by soaking the membrane/mesh in a polymer solution or melt or forcing the polymer solution or melt into the pores/holes under pressure. The membrane/mesh material may be permeable to the agent or impermeable to the agent. If it is permeable to the agent, agent will permeate through it to the environment of use at a given rate at temperatures below the melt temperature of the side-chain crystallizable polymer. At or above the melt temperature, the agent will permeate through both the membrane/mesh material and the side-chain crystallizable polymer filling the pores, thus providing a higher rate of agent release per unit of surface area. If the membrane/mesh material is impermeable to the agent, agent will not permeate through the membrane below the melt temperature of the side-chain crystallizable polymer. At or above that temperature, the agent will permeate through the membrane via the continuous pathways of side-chain crystallizable polymer.

The membrane or mesh may inherently be made of an electrically conductive material or be coated or contain particles of such a material (e.g., carbon, iron, nickel, copper, aluminum) by which the membrane/mesh may be heated by conduction or induction to cause the side-chain crystallizable material to undergo the desired phase change. When the diffusion matrix is intended to be heated by radiation, materials that enhance radiation absorption may be incorporated into the matrix.

It is also possible to disperse (blend homogenously) the side-chain crystallizable polymer at high volume loadings (e.g., greater than 20%, usually 50% to 90%) in a continuous or cocontinuous phase matrix material that is either permeable or impermeable to the agent. At such high volumes there are sufficient amounts of the dispersed side-chain crystallizable polymer to form continuous paths of side-chain crystallizable polymer through the matrix. In effect then, such dispersions function similarly to the embodiments in which the side-chain crystallizable polymer is suspended within a porous network or mesh. In this regard, it is necessary that the side chain crystallizable polymer be a continuous phase if the second polymer is impermeable to the agent to be delivered, and may be dispersed in the second polymer if the second polymer is essentially permeable to the agent to be delivered.

In a similar manner, a side chain crystallizable polymer may be immobilized by creating a second polymer within or throughout the side chain crystallizable polymer by polymerization and phase separation. For example, a non-crosslinked side chain crystallizable polymer may be heated above its melting point with a second monomer or monomer mixture and the monomer(s) caused to polymerize. In this case a supporting polymer network can be created in situ. In this case it is desirable that the second polymer created be at least partially insoluble in the side chain crystallizable polymer, yet be of a sufficient structure to bind the side chain crystallizable polymer into a stable form above its melting point.

In another form, a layer of side-chain crystallizable polymer is chemically bonded (grafted) to the surface of an agent-permeable polymer membrane. In this instance, the chemical bonding immobilizes the side-chain crystallizable polymer and prevents it from migrating out of the path of the agent. The side-chain crystallizable polymer may be grafted to the membrane surface through various functional groups as is known in the art. The particular surface treatments/bonding agents used will vary with the nature of the membrane and the side-chain crystallizable polymer.

The side chain crystallizable polymer may also be immobilized by sandwiching it between two agent-permeable polymer membranes that are fused to each other at a plurality of sites so as to prevent relative motion between the membranes when the side-chain crystallizable polymer melts. The fusions may be along continuous lines so as to form a wafer-like structure or be at separated points. Depending upon the thickness of the side-chain crystallizable layer in such assemblies it may be desirable to make such layer out of crosslinked side-chain crystallizable polymer to prevent the side-chain crystallizable polymer from oozing from the edge of the assembly.

The temperature controlled active agent dispensers of the invention may be of the dispersion or reservoir types described above. FIG. 1 depicts a simple dispersion type device, generally designated 11, which comprises a continuous matrix 12 of crosslinked side-chain crystallizable polymer in which particles of a diffusible active agent 13 are dispersed. At temperatures below the melt point of the polymer the permeability of the polymer to the agent is such that small or negligible amounts of active agents are released from the device. At temperatures at or above the melt point of the polymer, the permeability of the polymer to the agent increases dramatically and active agent dissolves in and diffuses through the polymer to the surface of the device and thence to the environment. The release rate of agent from such a device will be in accordance with Fick's Law and be proportional to time$^{-\frac{1}{2}}$. The duration of release will depend upon the configuration of the device and the amount of agent in the device.

Figure 2:
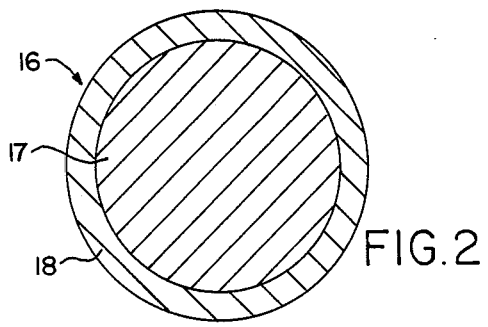
FIG. 2 is an enlarged, cross-sectional view of another embodiment of the invention in which active agent is encapsulated by a membrane of side-chain crystallizable material.

FIG. 2 shows an embodiment of a reservoir-type device, generally designated 16, in the form of a oapsule that comprises an active agent containing core 17 and an encapsulating membrane 18 of crosslinked side-chain crystallizable polymer. The core may be neat active agent or a mixture of active agent and a carrier or vehicle therefor. Typically, the core will comprise a combination of agent and carrier/vehicle and the amount of agent and its solubility in the carrier/vehicle will be such as to maintain unit activity throughout the intended lifetime of the device. In such embodiments (where unit activity is maintained) the release of active agent will be substantially constant and at a rate determined by the permeability of the membrane 18 to the agent. As in the case of device 11, when the device is maintained at a temperature below the melting point of the polymer, small or negligible release of agent occurs. At or above the melting point, significant release occurs. As an alternative to using a crosslinked side-chain crystallizable membrane, the membrane may be made of any of the above described diffusion matrices in which the side-chain crystallizable polymer is immobilized in a support, in a continuous matrix phase at high volume loading, or by chemical bonding to an agent-permeable membrane.

As in the case of device 11, materials may be included in the core and/or encapsulating membrane to facilitate or permit the device to be heated by radiation or electrical conduction/induction.

Figure 3:
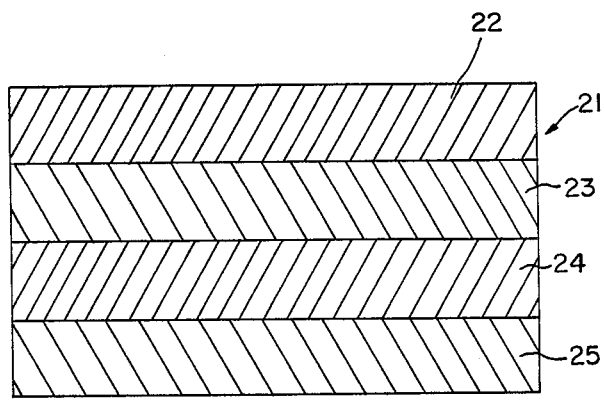
FIG. 3 is a cross-sectional view of another embodiment of the invention in which a membrane of side-chain crystallizable material is an element of a laminated composite.

FIG. 3 illustrates another type embodiment of a reservoir-type device, generally designated 21, in the form of a simple four-layer laminated composite, such as those used for transdermal administration of drugs. In this embodiment the side-chain crystallizable polymer diffusional barrier bounds the surface of the reservoir through which drug passes to the skin. The four layers of the device are: (1) an optional backing layer 22; (2) a drug reservoir layer 23; (3) a side-chain crystallizable polymer diffusion matrix layer 24; and (4) an optional pressure sensitive adhesive layer 25 that forms the basal layer of the device when it is in use. Prior to use the device will typically include a fifth removable release liner layer (not shown) that underlies the contact adhesive layer. The general mode of operation of such devices is well known in the medical device art and does not require detailed explanation. In this device the backing provides a protective layer and prevents dissemination of the drug from the upper surface of the reservoir. The reservoir serves as a source of drug and/or other agents such as skin permeation enhancing agents and may be composed solely of active ingredients or mixtures thereof in carriers. The diffusional matrix serves as the means for regulating the transport of drug from the reservoir to the skin. This matrix may be composed solely of crosslinked side-chain crystallizable polymer or one of the side-chain crystallizable polymer-containing matrices described above. As in the case of the devices of FIGS. 1 and 2, diffusion of drug through the polymer is small or negligible below the melting point of the polymer and substantial at or above the melting point. The pressure sensitive adhesive serves as a means for affixing the device to the skin. It may also serve as a supplemental reservoir for active ingredient. Other means, such as straps or elastic bands may be used in place of the adhesive to keep the device in contact with the skin.

Device 21 may contain means, such as an additional layer of conductive material, or conductive material dispersed in one or more of the layers, for heating the device at will. Alternatively, the device may be heated by placing an external source of heat on the device or by focusing radiation on the device. When the device is heated by electrical conduction or induction, the device may be cycled through the melting point of the polymer on command, thereby turning the flow of drug from the device to the skin on or off. Thus, virtually any pattern of drug release may be achieved.

The following examples further illustrate the invention. These examples are not intended to limit the invention in any manner. Unless indicated otherwise, percentages by weight are used in the examples.

EXAMPLE 1

Reservoir material was prepared by mixing 7.5 g of N,N dimethyl-p-toludine (NNDMPT) (Aldrich Chemical) with 45 g of ethylene-vinyl acetate copolymer (Elvax 260) (DuPont). Material was mixed thoroughly and allowed to imbibe for 24 hours. Material was then pressed into a 15 cm × 15 cm × 1.8 mm plaque at 120° C.

A device was fabricated from reservoir and Plexar 1 (Chemplex) with dimensions of 3.8 cm × 7.6 cm × 2.4 mm and having a reservoir surface area of 1.3 cm × 2 cm. A coarse weave polyester mesh 0.15 mm thick was laminated over the reservoir. A thin (approximately 0.13 mm) layer of recrystallized poly(vinyl stearate) (PVS) (Aceto Chemical) was then formed incorporating the mesh as a support. The device was put in distilled water for 16.5 hours with stirring to remove surface NNDMPT. The device was transferred to a clean beaker containing 200 ml of distilled water and maintained at 25° C. Periodically the U.V. absorbance (242 nm) was measured. This test procedure was repeated at 46°–47° C. and also for a device which was similar but had no PVS control membrane. The observed behavior is shown in Table I.

TABLE I

| Temperature °C. | Time (min.) | Absorbance | Rate (abs/min.) |
|---|---|---|---|
| Device with PVS Membrane | | | |
| 25 | 110 | 0.136 | $1.2 \times 10^{-3}$ |
| 48 | 105 | 0.463 | $4.4 \times 10^{-3}$ |
| 25 | 185 | 0.333 | $1.8 \times 10^{-3}$ |
| 45 | 60 | 0.310 | $5.2 \times 10^{-3}$ |
| 23 | 840 | 0.495 | $5.9 \times 10^{-4}$ |
| 23 | 410 | 0.262 | $6.4 \times 10^{-4}$ |
| 45 | 85 | 0.297 | $3.5 \times 10^{-3}$ |
| Control | | | |
| 25 | 10 | 0.1563 | $1.5 \times 10^{-2}$ |
| 25 | 25 | 0.2780 | $1.1 \times 10^{-2}$ |
| 25 | 40 | 0.4144 | $1.0 \times 10^{-2}$ |
| 25 | 70 | 0.6089 | $8.7 \times 10^{-3}$ |
| 25 | 90 | 0.7472 | $8.3 \times 10^{-3}$ |

This set of experiments show that PVS membranes exhibit distinct permeability behavior between 25° and 45° C. and that the effect is reversible.

EXAMPLE 2

Reservoir material was prepared by mixing 3 g of ferrocene (Aldrich Chemical) with 47 g of Elvax 40 (DuPont). This material was fabricated into a device which had an exposed reservoir surface of 1.5 cm × 3 cm.

A solution was prepared containing 97% octadecyl acrylate (Sartomer), 2.5% tri-propyleneglycol diacrylate and 0.5% benzoyl peroxide. Thin film of polyoctadecyl acrylate (PODA) were prepared by casting this solution onto heated glass plates (80°–120° C.) in a nitrogen atmosphere. The reservoir prepared above was covered with a section of this film and heat sealed. The release kinetics of this device in a 75:25 ethanol:water solution was measured by UV absorbance at 25° and 47° C. Results are given in Table II.

TABLE II

| Effect of Temperature on Release of Ferrocene By PODA Membrane | | |
|---|---|---|
| Temperature | Time (min) | Relative Rate |
| 25 | 10,320 | 1.0 |
| 47 | 160 | 129.0 |
| 25 | 21,480 | 0.70 |

The data show that polyoctadecyl acrylate transports ferrocene more than 100 times faster at 47° C. than at 25° C. and that this behavior is reversible. The experiments further show that thin films of crosslinked PODA can be laminated and heat sealed onto reservoirs and withstand solvents.

EXAMPLE 3

Reservoir material was prepared by combining 6.0 g of napthyl methyl carbamate (Carbaryl, Ortho) with 1 gram of acetylene black (a carbon black available from Gulf Canada) and 43 g of Elvax 260. The materials were mixed in a brabender at 100° C. and formed into a 15 cm × 15 cm × 2 mm plaque. A sample of reservoir material 2 cm × 2 cm was imbedded in an 2.0 mm sheet of Elvax 260 and one side sealed with Plexar 1 to give a device with 5 cm² of reservoir material exposed.

A solution was prepared consisting of 89% octadecyl acrylate, 5% tri-propyleneglycol diacrylate, 5% acrylic acid (Aldrich Chemical) and 1% Irgacure 184. The reservoir portion of the device was coated with 12 drops of solution and the solution cured into a thin coherent film by brief exposure to U.V. irradiation. The completed device was rinsed with warm isopropanol and soaked in ethanol to remove residual monomers.

Release kinetics of this device were measured in 200 ml solutions of ethanol at various temperatures as shown in Table III. Solution concentrations were determined by measuring the U.V. absorbance at 280 nm as a function of time. In each case the system exhibited nearly zero order kinetics. The rates given are the average over the duration of the experiment.

TABLE III

| Effect of Temperature on Release Kinetics of Carbaryl by PODA Membrane with Cycling | | | |
|---|---|---|---|
| Temperature °C. | Time (min) | Abs. (280 nm) | Rate (abs/min) |
| 25 | 107 | 0.1056 | $9.87 \times 10^{-4}$ |
| 44 | 35 | 0.7653 | $2.19 \times 10^{-2}$ |
| 30 | 100 | 0.1684 | $1.68 \times 10^{-3}$ |
| 21 | 150 | 0.0578 | $3.85 \times 10^{-4}$ |
| 44 | 40 | 0.855 | $2.14 \times 10^{-2}$ |
| 33 | 60 | 0.1926 | $3.21 \times 10^{-3}$ |

TABLE III-continued

| Effect of Temperature on Release Kinetics of Carbaryl by PODA Membrane with Cycling | | | |
|---|---|---|---|
| Temperature °C. | Time (min) | Abs. (280 nm) | Rate (abs/min) |
| 40 | 35 | 0.5409 | $1.54 \times 10 \text{ e-2}$ |
| 50 | 40 | 0.7403 | $1.85 \times 10 \text{ e-2}$ |

These data show that over the temperature range of 21° to 44° C. the rate of carbaryl transport by the PODA membrane increases by a factor of 55. Analysis of the data at shorter time intervals showed that the steady state rates showed an even greater change. A similar device with no rate controlling PODA membrane showed less than a two fold increase in rate from 25° to 44° C.

A comparison device was prepared as above except the reservoir surface was covered with a 0.25 mm film of Elvax 40 instead of PODA. The release kinetics were measured in ethanol as before and data is shown in Table IV.

TABLE IV

| Effect of Temperature on Release of Carbaryl by Elvax 40 Membrane | | | |
|---|---|---|---|
| Temperature | Time (min) | Abs. (280 nm) | Rate (abs/min) |
| 23 | 40 | 0.2744 | $6.86 \times 10 \text{ e-3}$ |
| 23 | 65 | 0.3813 | $5.87 \times 10 \text{ e-3}$ |
| 45 | 30 | 0.6005 | $2.00 \times 10 \text{ e-2}$ |

This result shows that diffusion of carbaryl through ethylene vinylacetate copolymer is only slightly dependent on temperature over the range of 23° to 45° C. In addition, this experiment shows that PODA is a very good diffusion barrier material at temperatures below its melting point.

EXAMPLE 4

Reservoir material was prepared by mixing 44 g of Elvax 250 and 6 g of Surflan. Surflan is a pre-emergence herbicide available from Elanco Products Company, division of Eli Lilly and Co., Indianapolis, IN. Devices were prepared by imbedding 2 cm×2 cm×1.1 mm portions of reservoir material into a 1.3 mm thick sheet of Elvax 260 which has 2 cm×2 cm holes cut in it. The resulting devices each had 8 cm² of exposed reservoir material. The exposed reservoir material was coated with a 0.13 mm thick film of U.V. curable resin prepared by mixing 4.96 g of PVS, 0.05 g of benzophenone (Aldrich Chemical) and 0.25 g of trimethylolpropane triacrylate (Sartomer). The film was cured by exposure to U.V. radiation.

Release kinetics in ethanol were determined by U.V. analysis at 24° C., 50° C. and 24° C. sequentially. The relative rates are given in Table V.

TABLE V

| Effect of Temperature on Release of Surflan by PVS Membrane | | | |
|---|---|---|---|
| Temperature °C. | Time (min) | Rate (abs/min) | Relative Rate |
| 24° C. | 1020 | $6.01 \times 10 \text{ e-5}$ | 1.0 |
| 50° C. | 50 | $1.44 \times 10 \text{ e-2}$ | 239.6 |
| 24° C. | 1100 | $8.75 \times 10 \text{ e-5}$ | 1.5 |

EXAMPLE 5

Diazinon is an organophosphate insecticide available from Ciba-Geigy Corporation, Agricultural Division, Greensboro, NC. A solution was prepared by mixing 1 gram of diazinon and 14 ml of ethanol. Celgard 2500 (Celanese Chemical Co.) was coated with a thin film of U.V. curable PVS (prepared as in the preceding example) and cured via exposure to U.V. radiation. A diffusion cell was prepared by mounting a small piece of coated film into a plastic holder with the aid of a rubber washer. The cell thus formed was filled with the diazinon solution and permeation rates of the membrane were measured as shown in Table VI.

TABLE VI

| Effect of Temperature on Permeation of Diazinon Through PVS Membrane | | | |
|---|---|---|---|
| Temperature °C. | Time (min) | Rate (abs/min) | Relative Rate |
| 21 | 1580 | $2.18 \times 10 \text{ e-5}$ | 1.0 |
| 45 | 100 | $3.57 \times 10 \text{ e-3}$ | 163.8 |
| 21 | 1260 | $5.16 \times 10 \text{ e-5}$ | 2.4 |
| 43 | 210 | $2.48 \times 10 \text{ e-3}$ | 113.8 |

EXAMPLE 6

Membrane material was prepared by coating and polymerizing a U.V. curable PVS solution in toluene onto Celgard 2500. A stock solution of nicotine was prepared by dissolving 2.0 g of nicotine base in 50 ml of distilled water. The nicotine solution was placed in a diffusion cell as described in the prior example and release properties were measured at 20° C. and 41° C. as shown in the following table VII.

TABLE VII

| Permeation of Nicotine Through PVS Membrane | | | |
|---|---|---|---|
| Temperature °C. | Time (min) | Rate (abs/min) | Relative Rate |
| 20 | 527 | $5.1 \times 10 \times \text{e-5}$ | 1 |
| 41 | 45 | $3.5 \times 10 \times \text{e-3}$ | 67 |
| 20 | 60 | $6.0 \times 10 \times \text{e-5}$ | 1.2 |

EXAMPLE 7

A resistive heating element was prepared as follows. A film obtained from Southwall Technology (Palo Alto, CA) which consisted of a polyester backing layer onto which had been deposited Indium Tin Oxide (ITO) with a top coat of Nickel. A portion of film 3 cm×7 cm was masked with masking tape and etched in 5N hydrochloric acid to expose a 1.5 cm×7 cm portion of the ITO. A thin film of cross-linked poly vinylstearate cured onto the exposed ITO was adherent and translucent when at room temperature. Application of 9 volts to the two nickel electrodes resulting in a current draw of approximately 0.1 amp and the polymer became transparent and tacky after 10 minutes, indicating that it was heated above its melting point. Removal of the power supply caused the polymer to become translucent and hard after about 5 minutes.

A nicotine-containing reservoir was prepared by mixing 1 gram of nicotine free base with 9 grams of Ucar Latex 173 (a commercially available emulsion of polyacrylate supplied by Union Carbide Corp. commonly used to prepare pressure sensitive adhesives) and coating this material onto an exposed portion of the ITO and allowing it to dry. This reservoir could be prepared in varying thicknesses and was tacky. An overcoat of poly vinylstearate was cured on top to the reservoir and an adhesive coating was applied to that using Ucar Latex 173. The device thus constructed was laminated to a thin (0.1 cm) sheet of foamed polystyrene to prevent heat loss from the backside. Similar insulating films of flexible materials such as foamed polyethylene are commercially available.

This device is useful for administering nicotine transdermally.

EXAMPLE 8

Another temperature-controlled nicotine dispenser was prepared as follows. A sample of Celgard 2500 was sputter coated with nickel to a resistivity of approximately 20 ohms/square. A 3 cm×5 cm portion of this film was etched to remove excess metal and electroded with a conductive epoxy adhesive to provide a porous heating element of 3 square cm area. This composite film was coated with poly octadecylmethacrylate from a toluene solution to allow the polymer to permeate into the porous structure and solvent was allowed to evaporate. This assembly was placed between a 10 ml reservoir containing 4% nicotine (w/w) and another reservoir containing 40 ml of water. The permeation rate of nicotine through the membrane was measured at 19° C. over a period of 110 minutes. A potential of 8 volts was applied to the device for a period of time resulting in a current of 0.185 amps. The permeation rate was measured while the device was powered and then the device was turned off. After a period of time the rate was again measured. This process was repeated several times. The release rates are given in Table VIII below.

TABLE VIII

| Device State | Rate (Abs/Min) | Relative Rate |
| --- | --- | --- |
| OFF (110 min.) | 0.00029 | 1.0 |
| ON (30 min.) | 0.0033 | 11.3 |
| OFF (180 min.) | 0.00043 | 1.5 |
| ON (20 min.) | 0.0032 | 11.0 |
| OFF (55 min.) | 0.00033 | 1.1 |
| ON (15 min.) | 0.0021 | 7.2 |
| OFF (90 min.) | 0.00037 | 1.3 |

EXAMPLE 9

Polymethyltetradecyl siloxane was obtained from Petrarch Systems Inc. 2.4 g of polymer, 0.1 g of t-butyl perbenzoate, 0.1 g of 1–6 hexanediol-diacrylate and 0.15 g of hexadecylacrylate were combined, coated onto Celgard 2500 and cured. Unreacted material was removed by soaking in alcohol for 48 hours.

A sample of this material was used as a membrane and the rate of diffusion of benzophenone from a 10% (w/v) ethanol volution was determined at a variety of temperatures as shown in Table IX.

TABLE IX

| Diffusion of Benzophenone Through Membrane | | |
| --- | --- | --- |
| Temperature °C. | Rate (mg/cm²/hr) | Relative rate |
| 5 | 0.015 | 1 |
| 10 | 0.053 | 3.4 |
| 15 | 0.70 | 46 |
| 20 | 0.98 | 64 |
| 25 | 1.30 | 80 |
| 10 | 0.13 | 2.4 |
| 15 | 0.79 | 46 |

Modifications of the above-described modes for carrying out the invention that are obvious to those of skill in polymer chemistry controlled release devices or related fields are intended to be within the scope of the following claims.

I claim:

1. A temperature controlled agent dispenser that provides a reversible, substantial change in agent dispensing rate at a selected temperature comprising a body that maintains its integrity at the selected temperature and is comprised of an agent and a side-chain crystallizable polymer which (i) is in a form that retains its shape and is not free to flow wholly at the selected temperature, (ii) exhibits a phase transition at the selected temperature, (iii) has substantially greater permeability to the agent at temperatures equal to or greater than the selected temperature than at temperatures below the selected temperature, and (iv) is interposed between the agent and an environment into which the agent is to be dispensed whereby the rate at which the agent is dispensed to the environment at a temperature equal to or greater than the selected temperature is dependent upon the rate at which the agent diffuses therethrough.

2. The dispenser of claim 1 wherein the side-chain crystallizable polymer defines at least a part of the exterior surface of the device.

3. The dispenser of claim 1 wherein said form constitutes a crosslinked side-chain crystallizable polymer.

4. The dispenser of claim 3 wherein the crosslinked side-chain crystallizable polymer has a heat of fusion of at least 5 cal/g and a crosslink density greater than 0.1.

5. The dispenser of claim 3 wherein the body comprises a dispersion of the agent in the crosslinked side-chain crystallizable polymer.

6. The dispenser of claim 1 wherein the body comprises a core of the agnt bounded wholly or partly by a membrane of the side-chain crystallizable polymer.

7. The dispenser of claim 6 wherein the core comprises a mixture of the agent and a vehicle or carrier therefor.

8. The dispenser of claim 7 wherein the relative amounts of agent and carrier in the core and the solubility of the agent in the vehicle or carrier are such as to maintain unit activity during the dispensing lifetime of the device.

9. The dispenser of claim 3 wherein the body comprises a core of the agent bounded wholly or partly by a membrane of the crosslinked side-chain crystallizable polymer.

10. The dispenser of claim 1 wherein the body comprises a laminated composite one of the laminas of which is composed of a dispersion of the agent in the side-chain crystallizable polymer.

11. The dispenser of claim 1 wherein the body comprises a laminated composite one of the laminas of which is composed of a mixture of the agent and a vehicle or carrier therefor and another of the laminas is composed of the side-chain crystallizable polymer.

12. The dispenser of claim 10 wherein the agent is a drug and the dispenser is for administering the drug transdermally.

13. The dispenser of claim 12 wherein the laminated composite includes a backing lamina and a pressure sensitive adhesive lamina for affixing the dispenser to the skin.

14. The dispenser of claim 11 wherein the agent is a drug and the dispenser is for administering the drug transdermally.

15. The dispenser of claim 14 wherein the laminated composite includes a backing lamina and a pressure sensitive adhesive lamina for affixing the dispenser to the skin.

16. The dispenser of claim 1 including electrical conducting means for heating the dispenser by conduction or induction.

17. The dispenser of claim 1 including radiation absorbing means for facilitating heating the dispenser with radiation.

18. The dispenser of claim 10 including electrical conducting means for heating the dispenser by conduction or induction.

19. The dispenser of claim 18 wherein the means is a lamina of an electrical conducting material.

20. The dispenser of claim 11 including electrical conducting means for heating the dispenser by conduction or induction.

21. The dispenser of claim 20 wherein the means is a lamina of an electrical conducting material.

22. A temperature-controlled diffusional matrix for regulating transport of an agent from a source of the agent to an environment of use for the agent comprising a body of (a) a solid support phase and (b) a side-chain crystallizable polymer phase which (i) exhibits a phase transition at a selected temperature and (ii) has substantially greater permeability to the agent at temperatures equal to or greater than the selected temperature than at temperatures below the selected temperature, wherein there is at least one continuous path through the body that is defined by the side-chain crystallizable polymer phase and the side-chain crystallizable polymer is immobilized.

23. The diffusional matrix of claim 22 wherein the solid support phase is made of a material that is permeable to the agent.

24. The diffusional matrix of claim 22 wherein the solid support phase is made of a material that is impermeable to the agent.

25. The diffusional matrix of claim 22 including electrical conducting means for heating the matrix by conduction or induction.

26. The diffusional matrix of claim 22 wherein the solid support phase is a microporous membrane and the side-chain crystallizable polymer is within the pores of the membrane.

27. The diffusional matrix of claim 22 wherein the solid support is a mesh and the side chain crystallizable polymer is within the holes of the mesh.

28. The diffusional matrix of claim 22 wherein the solid support phase is continuous and the side-chain crystallizable polymer is dispersed in the solid support phase at a volume loading above about 20%.

29. A temperature-controlled diffusion matrix for regulating transport of an agent from a source of the agent to an environment of use for the agent comprising (a) an agent-permeable polymer membrane and (b) a layer of side-chain crystallizable polymer grafted to the surface of the membrane, the side-chain crystallizable polymer (i) exhibiting a phase transition at a selected temperature and (ii) having substantially greater permeability to the agent at temperatures equal to or greater than the selected temperature than at temperatures below the selected temperatures.

30. A temperature-controlled diffusion matrix for regulating transport of an agent from a source of the agent to an environment of use for the agent comprising a laminated composite of (a) a layer of side-chain crystallizable polymer that (i) exhibits a phase transition at a selected temperature and (ii) has substantially greater permeability to the agent at temperatures equal to or greater than the selected temperature than at temperatures below the selected temperatures sandwiched between (b) layers of an agent-permeable polymer that are bonded to each other to prevent relative motion therebetween.

* * * * *

UNITED STATES PATENT AND TRADEMARK OFFICE
CERTIFICATE OF CORRECTION

PATENT NO. : 4,830,855

DATED : May 16, 1989

INVENTOR(S) : Ray F. Stewart

It is certified that error appears in the above-identified patent and that said Letters Patent is hereby corrected as shown below:

Title page, In Abstract, line 11, change "tempertures" to --temperatures--.

Column 2, line 44, change "Cone" to --One--.

Column 5, line 55, change "material" to --materials--.

Column 10, line 10, change "film" to --films--.

Column 14, line 31, change "agnt" to --agent--.

Signed and Sealed this

Seventeenth Day of April, 1990

Attest:

HARRY F. MANBECK, JR.

*Attesting Officer*      *Commissioner of Patents and Trademarks*